(12) United States Patent
Mantegani et al.

(10) Patent No.: US 6,407,122 B1
(45) Date of Patent: Jun. 18, 2002

(54) AMINO-BENZOTHIAZOLE DERIVATIVES

(75) Inventors: Sergio Mantegani, Milan; Paolo Cremonesi, Melzo; Mario Varasi, Milan; Carmela Speciale, Nerviano, all of (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

(21) Appl. No.: 09/554,612

(22) PCT Filed: Nov. 23, 1998

(86) PCT No.: PCT/EP98/07532

§ 371 (c)(1),
(2), (4) Date: Jun. 1, 2000

(87) PCT Pub. No.: WO99/28318

PCT Pub. Date: Jun. 10, 1999

(30) Foreign Application Priority Data

Dec. 2, 1997 (GB) ................................. 9725541

(51) Int. Cl.$^7$ ..................... A61K 31/445; C07D 417/12
(52) U.S. Cl. ........................................ 514/321; 546/198
(58) Field of Search ........................... 514/321; 546/198

(56) References Cited

FOREIGN PATENT DOCUMENTS

WO        WO-9/14444        * 4/1998

OTHER PUBLICATIONS

Burlakova "Antioxidant drugs as neuroprotective agents" CA 123:218179 (1995).*
Jarrot et al. "Development of a novel arylalkylpiperazine compound as a hybride neruroprotective drug" CA 131:138817 (1999).*
Bebbington et al. "Synergistic dual mechanism antioxidants . . . " CA 2000:331694 (2000).*

* cited by examiner

*Primary Examiner*—Ceila Chang
(74) *Attorney, Agent, or Firm*—Oblon, Spivak, McClelland, Maier & Neustadt, P.C.

(57) ABSTRACT

The present invention relates to amino-benzothiazole compounds of formula (I)

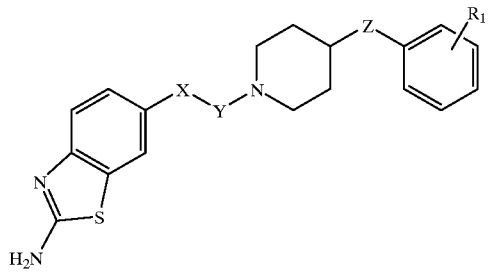

wherein X, Y, Z and $R_1$ are as defined in the specification, their pharmaceutically acceptable salts, processes for their preparation, pharmaceutical composition comprising such compounds and their use as neuroprotective agents.

8 Claims, No Drawings

AMINO-BENZOTHIAZOLE DERIVATIVES

This application is a 371 of PCT/EP98/07532 filed Nov. 23, 1998.

The present invention relates to novel aminobenzothiazole derivatives, to a process for their preparation, to pharmaceutically acceptable compositions comprising them and to the use of said compounds in the prevention and/or treatment of acute or chronic neurodegenerative disorders.

According to W. Danysz et al., DN&P 8(5), June 1995, excitatory amino acid (EAA) glutamate is a broad spectrum agonist at the major neuronal EAA receptor sites. Although glutamate is a very important element in governing physiological balance within the central nervous system (CNS), under certain conditions excessive activation of glutamate receptors is neurotoxic. It is now clear that not only exogenously given excitotoxins but also endogenous glutamate or other similar agonists can kill neurons under certain pathological conditions called "excitotoxicity". It has been implied that excitotoxicity is involved in many types of acute neurodegenerative disorders such as, for example, ischemia, hypoglycemia or hypoxia and chronic neurodegenerative disorders such, for example, Huntington's, Parkinson's and Alzheimer's diseases, AIDS-dementia, hepatic encephalopaty, amyotrophic lateral sclerosis, epilepsy-related damage, olivopontocerebellar atrophy, Tourette's syndrome, CNS pathology related to measles virus, infection and motor neuron disease.

Agents able to modulate or antagonize the neurotoxic effect of an endogenous excitatory amino acid (EAA) or a similar compound at the CNS level can therefore be useful as neuroprotective agents for the prevention and/or treatment of an acute or a chronic neurodegenerative disease.

There is therefore a need to find pharmacological substances which exert a control of the above mentioned neuropathological processes by means of their activity as mediators or inhibitors of the effects of said neurotoxic agents.

The present invention fulfill such a need.

Accordingly, the present invention provides a 2-aminobenzothiazole derivative of formula (I)

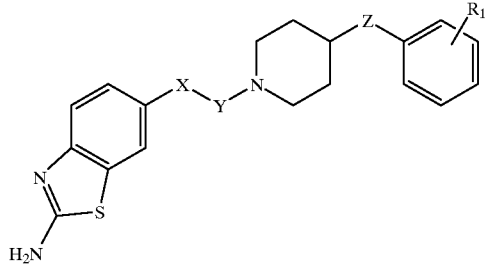

(I)

if the case either as single isomer or as mixture of isomers, wherein

X is CO, C=NOH, CHOH or $CH_2$;

Y is $CH_2$ or
  $CHCH_2R_2$ in which
    $R_2$ is hydrogen, hydroxy, phenoxy, amino, $N(CH_3)_2$, $OCOR_4$ in which $R_4$ is $C_1$–$C_6$ alkyl or a group of formula (i)

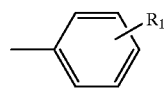

(i)

wherein $R_1$ is hydrogen, halogen, cyano, a linear or branched $C_1$–$C_5$ alkyl group, a linear or branched $C_1$–$C_5$ alkoxy group or trifluoromethyl; or $R_2$ is $NHR_3$ in which $R_3$ is a linear or branched $C_2$–$C_6$ alkanoyl group, a linear or branched $C_1$–$C_6$ alkylsulfonyl group, trifluoromethanesulfonyloxy, or a group of formula (i) or (ii)

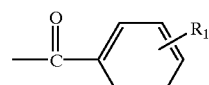

(ii)

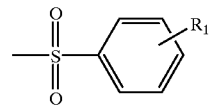

(iii)

wherein $R_1$ is as defined above;

Z is a $(CH_2)_n$ group wherein n is zero or an integer from 1 to 4; CHOH; CO; O; S; $SO_2$ or a group of formula (iv)

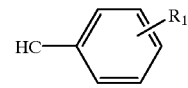

(iv)

wherein $R_1$ is as defined above;
provided that :
  when X is CO, $R_2$ is not hydroxy;
or a pharmaceutically acceptable salt thereof.

Depending on the precise meaning of the substituent(s) X and/or Y, the compounds of formula(I) can have one or more asymmetric centers and therefore can exist in different stereoisomers. For example, a compound of formula (I) which possesses one asymmetric center can exist either as a pure optical isomer or as racemic mixture; and a compound of formula (I) which possesses two, not equivalent, asymmetric centers wherein one of the substituents is the same, can exist as a threo or an erithro pure optical isomer or as threo or erithro racemic mixture.

Both the racemic mixture and the pure optical isomers of a compound of formula (I) are within the scope of the invention.

The present invention further comprises pharmaceutically acceptable salts of the compounds of formula (I) with pharmaceutically acceptable inorganic acids such as, e.g., hydrochloric, hydrobromic, sulfuric, nitric or phosphoric acid and organic acids such as, e.g., malic, maleic, pamoic, succinic, gluconic, citric, tartaric, ascorbic, acetic, methanesulphonic or benzensulphonic acid.

A linear or branched $C_2$–$C_6$ alkyl group may be, for example, methyl, ethyl, n-propyl, iso-propyl, n-butyl sec-butyl, tert-butyl or n-pentyl; preferably it is methyl, ethyl or n-propyl.

A linear or branched $C_1$–$C_5$ alkoxy group may be, for example, methoxy, ethoxy, n-propoxy, iso-propoxy, n-butoxy or sec-butoxy; preferably, it is methoxy or ethoxy.

A linear or branched $C_2$–$C_4$ alkanoyl group may be, for example, acetyl, propanoyl, isobutirroyl, valeroyl; preferably, it is acetyl or propanonyl.

A linear or branched $C_1$–$C_6$ alkylsulfonyl group may be, for example, methanesulphonyl, ethanesulphonyl or propanesulphonyl; preferably, it is a linear $C_1$–$C_3$ alkylsulfonyl group, in particular methanesulphonyl ot ethanesulphonyl.

In a group of formula (i), (ii), (iii) or (iv), the substituent $R_1$, which may be in position orto, meta, or para of the phenyl ring is, preferably, in position para.

Preferably, $R_1$ is hydrogen or halogen, in particular fluorine.

A preferred class of compounds of the invention are compounds of formula (I), if the case either as single isomers or as mixture of isomers, wherein X is CO, CHOH or $CH_2$;

Y is $CH_2$ or $CHCH_2R_2$ wherein $R_2$ is hydrogen, hydroxy, phenoxy, $N(CH_3)_2$ or wherein $R_2$ is $NHR_3$ in which $R_3$ is a linear $C_1$–$C_3$ alkylsulfonyl group, a group of formula (ii) or (iii) as defined above in which $R_1$ is hydrogen;

Z is a $(CH_2)_n$ group wherein n is 1, CO, O, S or a group of formula (iv) as defined above in which $R_1$ is hydrogen or halogen;

$R_1$ is as defined above;

provided that:

when X is CO, Y is not hydroxy; and the pharmaceutically acceptable salts thereof.

Examples of specific compounds of the invention are:
1) 1-Hydroxymethyl-1-(4-benzylpiperidin-1-yl)-2-hydroxy-2-(2-aminobenzothiazol-6-yl)-ethane;
2) 1-Phenoxymethyl-1-(4-benzylpiperidin-1-yl)-2-hydroxy-2-(2-aminobenzothiazol-6-yl)-ethane;
3) 1-Dimethylaminomethyl-1-(4-benzylpiperidin-1-yl)-2-hydroxy-2-(2-aminobenzothiazol-6-yl)-ethane;
4) 1-Benzoylaminomethyl-1-(4-benzylpiperidin-1-yl)-2-hydroxy-2-(2-aminobenzothiazol-6-yl)-ethane;
5) 1-Methanesulphonylaminomethyl-1-(4-benzylpiperidin-1-yl)-2-hydroxy-2-(2-aminobenzothiazol-6-yl)-ethane;
6) 1-Phenylsulphonylaminomethyl-1-(4-benzylpiperidin-1-yl)-2-hydroxy-2-(2-aminobenzothiazol-6-yl)-ethane;
7) 1-(2-Amino-benzothiazol-6-yl)-2-(4-benzyl-piperidin-1-yl)-propan-1-ol;
8) 1-(2-Amino-benzothiazol-6-yl)-2-(4-benzyl-piperidin-1-yl)-propane;
9) 1-(2-Amino-benzothiazol-6-yl)-2-(4-benzyl-piperidin-1-yl)-ethane;
10) 1-(2-Amino-benzothiazol-6-yl)-2-(4-phenoxy-piperidin-1-yl)-ethane;
11) 1-(2-Amino-benzothiazol-6-yl)-2-(4-phenylthio-piperidin-1-yl)-ethane;
12) 1-(2-Amino-benzothiazol-6-yl)-2-(4-benzoyl-piperidin-1-yl)-ethane;
13) 1-(2-Amino-benzothiazol-6-yl)-2-(4-(4,4'-difluorodiphenylmethyl-piperidin-1-yl)-ethane;
14) 1-(2-Amino-benzothiazol-6-yl)-3-phenoxy-2-(4-benzyl-piperidin-1-yl)-propan-1-one;
15) 1-(2-Amino-benzothiazol-6-yl)-3-dimethylamino-2-(4-benzyl-piperidin-1-yl)-propan-1-one;
16) 1-(2-Amino-benzothiazol-6-yl)-3-benzoylamino-2-(4-benzyl-piperidin-1-yl)-propan-1-one;
17) 1-(2-Amino-benzothiazol-6-yl)-3-methanesulphonylamino-2-(4-benzyl-piperidin-1-yl)-propan-1-one;
18) 1-(2-Amino-benzothiazol-6-yl)-3-phenylsulphonylamino-2-(4-benzyl-piperidin-1-yl)-propan-1-one;
19) 2-(4-Benzylpiperidin-1-yl)-1-(2-amino-benzothiazol-6-yl)-propan-1-one;
20) 2-(2-Benzoylpiperidin-1-yl)-1-(2-aminobenzothiazol-6-yl)-propan-1-one;
21) 1-(2-Aminobenzothiazol-6-yl)-2-(4-benzyl-piperidin-1-yl)-ethanone;
22) 1-(4-Benzoylpiperidin-1-yl)-2-(2-amino-benzothiazol-6-yl)-ethanone;
23) 1-(4-Phenoxypiperidin-1-yl)-2-(2-amino-benzothiazol-6-yl)-ethanone;

and their pharmaceutically acceptable salts;

if the case, when one asymmetric center is present on the molecule, either as a pure optical isomer or as racemic mixture; or when two, not equivalent, asymmetric centers wherein a substituent is the same, are present on the molecule, either as a threo or an erithro pure optical isomer or as threo or erithro racemic mixture.

A compound of formula (I), if the case, either as pure optical isomer or as racemic mixture, can be prepared by a process which comprises:

a) reacting a compound of formula (II)

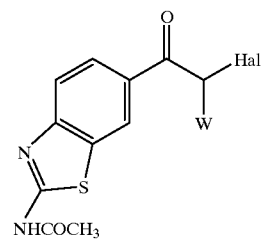

(II)

if the case, either as pure optical isomer or as racemic mixture, wherein W is hydrogen or methyl and Hal is a halogen atom;

with a compound of formula (III)

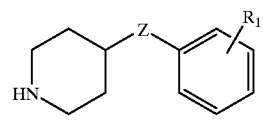

(III)

wherein

Z is a $(CH_2)_n$ group wherein n is zero or an integer from 1 to 4, CHOH, CO, O, S, $SO_2$ or a group of formula (iv)

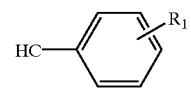

(iv)

wherein $R_1$ is hydrogen, halogen, cyano, a linear or branched $C_1$–$C_5$ alkyl group, a linear or branched $C_1$–$C_5$ alkoxy group or trifluoromethoxy;

to obtain a compound of formula (I), if the case, either as a pure optical isomer or as racemic mixture, wherein Z and $R_1$ are as defined above, X is CO and Y is $CH_2$ or $CHCH_2R_2$ in which $R_2$ is hydrogen; and, if desired, b) converting a compound of formula (I) as obtained under step a), into another compound of formula (I) wherein Y, Z and $R_1$ are as defined above and X is CHOH; or c) converting a compound of formula (I) as obtained under step a), into another compound of formula (I) wherein Y, Z and $R_1$ are as defined above and X is $CH_2$; or d) converting a compound of formula (I) as obtained under step a), into another compound of formula (I) wherein Y, Z and $R_1$ are as defined above and X is C=NOH; or e) condensing a compound of formula (IV)

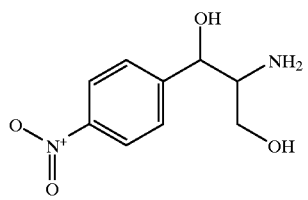

(IV)

if the case, either as pure optical isomer or as racemic mixture, with a compound of formula (V)

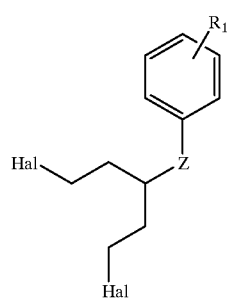

(V)

wherein Hal, Z and $R_1$ are as defined above, to obtain a compound of formula (VI)

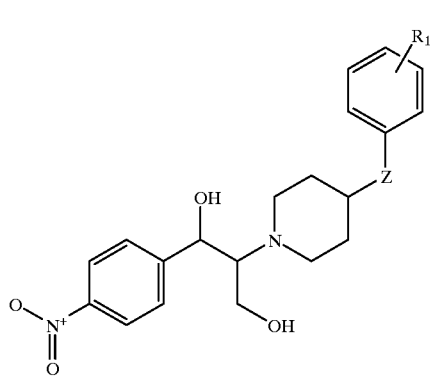

(VI)

if the case either as a pure optical isomer or as racemic mixture, wherein Z and $R_1$ are as defined above;

f) converting a compound of formula (VI) as obtained under step e), to obtain a compound of formula (VII)

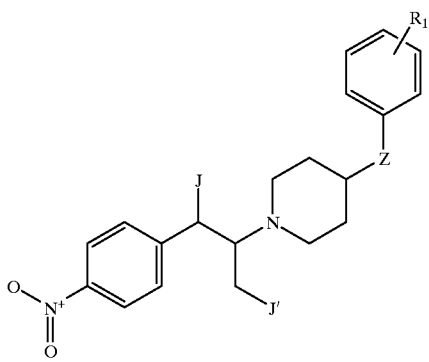

(VII)

if the case either as a pure optical isomer or as racemic mixture, wherein Z and $R_1$ are as defined above, J is hydroxy or phenylthio and J' is amino, $N(CH_3)_2$ phenoxy, phenylthio, $OCOR_4$ in which $R_4$ is $C_1$–$C_6$ alkyl or a group of formula (i)

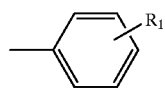

(i)

wherein $R_1$ is as defined above, or J' in $NHR_3$ in which $R_3$ is a linear or branched $C_2$–$C_6$alkanoyl group, a linear or branched $C_1$–$C_6$ alkylsulfonyl group, trifluoromethanesulphonyloxy or a group of formula (ii) or (iii)

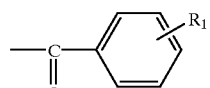

(ii)

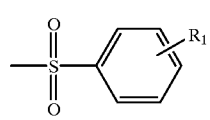

(iii)

wherein $R_1$ is as defined above;

g) reducing a compound of formula (VII) to obtain a compound of formula (VIII)

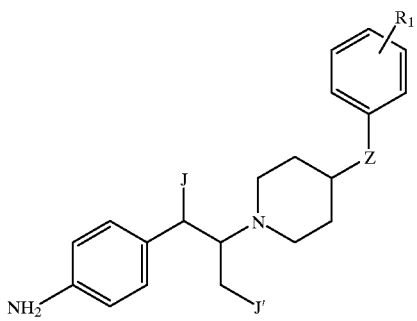

(VIII)

if the case, either as a pure optical isomer or as racemic mixture, wherein J is hydroxy or hydrogen, Z and $R_1$ are as defined above and J' is hydrogen, phenoxy, $N(CH_3)_2$, $OCOR_4$ in which $R_4$ is as defined above, or J' is $NHR_3$ in which $R_3$ is as defined above;

h) converting a compound of formula (VIII) into a compound of formula (I), if the case, either as a pure optical isomer or as racemic mixture, wherein Z and $R_1$ are as defined above, X is CHOH or $CH_2$ and Y is $CHCH_2R_2$ in which $R_2$ is hydrogen, phenoxy, $N(CH_3)_2$, $OCOR_4$ in which $R_4$ is as defined above, or J' is $NHP_3$ in which $R_3$ is as defined above; and, if desired, i) converting a compound of formula (I) if the case, either as a pure optical isomer or as racemic mixture, wherein Z, $R_1$ and X are as defined above and Y is $CHCH_2R_2$ wherein $R_2$ is $NHR_3$ in which $R_3$ is a linear or branched $C_2$–$C_6$ alkanoyl group or a group of formula (ii) as defined above, into another compound of formula (I) wherein Z, $R_1$ and X are as defined above and Y is $CHCH_2R_2$ wherein $R_2$ is amino, and, if desired, j) converting a compound of formula (I) as obtained under step h) or i) into another compound of formula (I) wherein Y, Z and $R_1$ are as defined above and X is C=O—;

and, if desired, converting a compound ot formula (I) into a pharmaceutically acceptable salt thereof.

In a compound of formula (II) or (V) a halogen atom is bromine, chlorine or iodine; preferably it is bromine.

When a compound of formula (IV) is an optically pure threo or erithro isomer, the whole synthetic procedure do not affect the chirality of the stereo center/s which is/are mantained on the end product.

The reaction described as step al comprises a nucleophilic displacement of a suitable α-halogen ketone of formula (II) with a piperidine derivative of formula (III), followed by the amide hydrolysis.

The nucleophilic displacement can be carried out, for example, in presence of a proton scavenger such as, e.g., triethylamine (TEA), $K_2CO_3$ or ethyldiisopropylamine (Hünig's base), in a solvent such as, e.g., dimethylformamide (DMF), dimethylsolfoxide (DMSO), EtOH or tetrahydrofuran (THF), at a temperature ranging from about 40° C. to about 100° C.

The amide hydrolysis is generally carried out with a base such as, e.g., 1 M NaOH solution or $K_2CO_3$, in a solvent such as, e.g. EtOH or dioxane, at a temperature ranging from about 50° C. to about 110° C.

The conversion of a compound of formula (I) as obtained in step a), into another compound of formula (I) wherein X is CHOH, described as step b), may be carried out, for example, by employing a reducing agent such as, e.g. $LiAlH_4$, in a solvent such as, e.g., THF, diethyl ether or dioxane, or employing a reducing agent such as, e.g. $NaBH_4$, in a solvent such as, e.g., THF, dioxane, ethanol or isopropanol, at a temperature ranging from about −5° C. to about 35° C.; preferably, the reaction described as step b) may be performed by using $NaBH_4$ in ethanol, at a temperature ranging from about −5° C. to about 35° C.

The conversion of a compound of formula (I) as obtained in step a), into another compound of formula (I) wherein X is $CH_2$, described as step c), may be carried out, for example, by employing as reducing agent, e.g. triethylsilane in trifluoroacetic acid, at a temperature ranging from about −15° C. to about 25° C.

The conversion of a compound of formula (I) as obtained in step a), into another compound of formula (I) wherein X is C=NOH, described as step o) may be carried out, for example, by reaction with hydroxylamine hydrochloride in pyridine or in presence of a proton scavenger such as, e.g. sodium acetate in ethanol/water, at a temperature ranging from about 25° C. to about 80° C.

Alternatively, a compound of formula (I) wherein X is $CH_2$; Y is $CH_2$ or $CHCH_2R_2$ in which $R_2$ is hydrogen; $R_1$ is hydrogen, halogen, cyano, a linear or branched $C_1$–$C_5$ alkyl group, a linear or branched $C_{1-5}$ alkoxy group or trifluoromethyl and Z is a $(CH_2)_n$ group wherein n is zero or an integer from 1 to 4, CHOH, CO, O, S, $SO_2$ or a group of formula (iv)

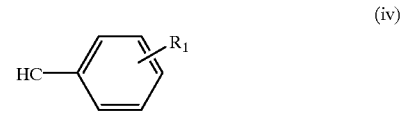

(iv)

wherein $R_1$ is as defined hereabove, may be obtained reacting a compound of formula (IX)

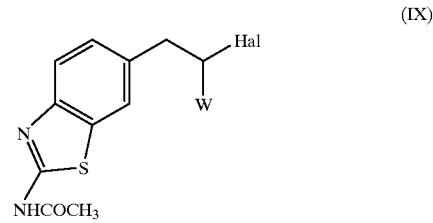

(IX)

wherein W is hydrogen or methyl and Hal is a halogen atom, preferably a bromine atom, with a compound of formula (III) as defined above, in the presence of a base such as, e.g., TEA, $K_2CO_3$ or ethyldiisopropylamine, in a solvent such as, e.g. ethanol or DMF, at a temperature ranging from about 25° C. to about 75° C., further hydrolysing the amide group by saponification, for example, by means of a base such as, e.g. KOH or $K_2CO_3$, in a solvent such as, e.g. ethanol or THF, at a temperature ranging from about 35C° C. to about 75° C.

The condensation of a compound of formula (IV) with a compound of formula (V) described as step e) may be carried out, for example, in presence of a base such as, e.g., TEA, Hünig's base or $K_2CO_3$, in a solvent such as, e.g. DMF or dioxane, at a temperature ranging from about 50° C. to about 100° C.

The conversion described as step f) may be carried out, for example, by reacting a compound of formula (VI) with triphenylphosphine/diethylazodicarboxilate/phenol, triphenylphosphine/diethylazodicarboxilate/phtalimide, diphenyldisulfide/tributylphosphine or triphenylphosphine/diethylazodicarboxylate/$R_4$° COOH wherein $R_4$ is as defined above, in a solvent such as, e. g. THF or dioxane, at a temperature ranging from about 20° C. to about 100° C.

In particular, a compound of formula (VII) wherein J' is an amino group may be obtained by reaction of a compound of formula (VI) with triphenylphosphine/diethylazodicarboxilate/phalimide, further adding to the reaction mixture hydrazine hydrate in ethanol at 50° C.

When in a compound of formula (VII) J' is amino, it can be further transformed into a group of formula $NHR_3$, wherein $R_3$ has the meanings before mentioned,for example, by reaction with an appropiate $C_2$–$C_6$ alkanoyl, $C_1$–$C_6$ alkylsulfonyl or trifluoromethanesulphonyl halide or a suitable campound of formula (X) or (XI)

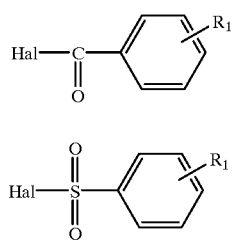

wherein Hal is a halogen atom, preferably chlorine and $R_1$ is as defined above, in a solvent such as, e.g. pyridine or dichloromethane in presence of TEA, at a temperature ranging from about 0° C. to about 35° C.

The reduction described as step g) may be carried out, for example, by means of a reducing agent such as, e.g. Fe or Zn in hydrochloric acid; $SnCl_2$ in a hydrochloric acid solution; or by a catalitic hydrogenation, for example with hydrogen, in presence of a catalyst such as, e.g. Pd/C, in a solvent such as e.g. ethanol, at a pressure which may vary from about 1 atm to about 5 atm, at a temperature ranging from 25° C. to 50° C.

In particular, when reducing a compound of formula (VII) wherein J and J' are both phenylthio, a compound of formula (VIII) wherein J is hydrogen and J' is hydrogen can be obtained. Preferably, this reduction is accomplished by catalytic hydrogenation at about 2 atm employing Nickel Raney as a catalyst, in a solvent such as, e.g. ethanol.

The conversion described as step h) may be carried out, for example, by reaction with $(SCN)_2$, generated by action of, e.g. $Br_2$ or $CuSO_4$ on KSCN in glacial acetic acid, at a temperature of about 25° C.

The conversion described as step i) may be carried out, for example with a base, for example an inorganic base such as, e.g., NaOH or $K_2CO_3$ in a solvent such as, e.g. EtOH or dioxane, at a temperature ranging from about 50° C. to about 110° C.

The conversion of a compound of formula (I) wherein X is CHOH into another compound of formula (I) wherein X is C=O described under step j) may be carried out, for example, by reaction with DMSO/ trifluoroacetamide (TFAA)/TEA at c temperature ranging from about −78° C. to about 0° C.

The conversion of a compound of formula (I) into a pharmaceutically acceptable salt thereof may be carried out following procedures well known in the art. For example, a pharmaceutically acceptable salt of a compound of formula (I) may be obtained combining a compound of formula (I) with at least one molar equivalent of a suitable pharmaceutically acceptable acid as defined above, in a solvent such as, e.g, ethanol or chloroform.

As stated above, the compounds of formula (I) can exist in different stereoisomers.

The stereoisomers can be separated from he corresponding mixture of stereoisomers, following methods well known in the art. For example, the racemate can be resolved into the two enantiomers by crystallization of the diastereomeric acid addition salts obtained via an optically active acid such as, e.g., tartaric, dibenzoyltartaric, camphoric or camphorsulphonic acid. In particular, when in a compound of formula (I) the substituent X is CHOH, the racemic mixture can be resolved by conversion into the diastereomeric ester or carbamate using an appropriate optically active activated acid derivative or isocyanate. After separation of the diastereoisomers by crystallization or chromatography, the pure enantiomers are recovered by saponification or by alcoholysis.

In alternative, the optically active compounds of formula (I) can be prepared in a stereoselective manner either starting from optically pure material or using optically active reagents, following methods widely reported in literature.

Both the racemic mixtures and the pure optical isomers of the compounds of formula (I) are within the scope of the invention.

The compounds of formula (II) can be prepared following procedures well known in the art starting from commercially available compounds.

The compounds of formula (III) are commercially available compounds or can be prepared following procedures well known in the art starting from commercially available compounds.

The compounds of formula (IV) are commercially available compounds.

The compounds of formula (IX) (X) and (XI) can be prepared following procedures well known in the art starting from commercially available compounds.

The compounds of formula (I) and their pharmaceutically acceptable salts possess selective neuroprotective activity.

The efficacy of the compounds of the invention as neuroprotective agents was evaluated in mixed cortical neuronal cultures, following the method reported below.

Mixed cortical neuronal cultures from foetal rats at 16 days of gestation were prepared as described by Choi (j. Neur. Sci. 7: 357–368, 1987). Briefly dissociated cells were plated on poly-L-lysine coated multiwell plates at density of $1*10^5$ cells/$cm^2$ in MEM with Earle's salts supplemented with 21 mM D-glucose, 2 mM L-glutamine, 50 µg/ml Streptomicin, 50 IU Penicillin, 10% Foetal Calf Serum and 10% Horse Serum. Cultures were kept at 37° C., 5% $CO_2$ and survived about 5 weeks. After 7 days in vitro, astrocites proliferation was inhibited by adding 10 µM Cytosine Arabinoside for 48 hours; the medium was subsequently substituted twice a week with a fresh medium without foetal call serum (Hatley, J. Pharm. and Exp. Ther. 250 (II);752–758, 1989).

Only nature cortical cultures, from 14 DIV on, were used for the study. Experiments were performed at 25° C. as follows: cells were washed once with a Locke's buffer, (128 mM NaCl, 25 nM KCl, 1.2 mM $Na_2HPO_4$, 2.7 mM $CaCl_2$, 20 mM Hepes and 10 mM D-glucose) pH=7.4, then preincubated with the test compounds for 3 min. followed by a 20 min. exposure to N-methyl-D-aspartate (NMDA) (500 µM).

The incubation was stopped by removing Locke's buffer and substituting the conditioned medium. After 24 hours at 37° C., 5% $CO_2$, Trypan Blue Dye Exclusion Test (0.04%) was used for evaluating the cells viability.

As an example, the neuroprotective effects in the above cultured cortical neurons of 1-(2-Amino-$^{benzothiazol-6-yl}$)-2-(4-benzyl-piperidin-1-yl)-ethane (compound of Example 15), were tested in comparision with the neuroprotective effects of Eliprodil, a known neuroprotective agent.

The obtained results are reported in the following Table 1.

TABLE 1

| COMPOUND | $EC_{50}$ (µM)* |
|---|---|
| Eliprodil | 2.26 |
| Example 15 | 0.64 |

*EC50 values were the mean of at least 3 different experiments

The above tabulated data clearly demonstrate, not only that the representative compound of the present invention is particularly effective as neuroprotective agent by virtue of its ability to prevent the neurotoxic action of the EAA glutamic acid, but also that its neuroprotective activity is superior (more than three times) than that one exibited by the reference compound Eliprodil.

For the above reasons, the compounds of the present invention can be useful as neuroprotective agents in the prevention and/or treatment of an acute or a chronic neurodegenerative disease, associated with the neurotoxic effect of an EAA or a similar compound. For example, the compounds of the present invention can be useful in the prevention and/or treatment of an acute neurodegenerative disorder such as, for example, ischemia, hypoglycemia or hypoxia and chronic neurodegenerative disorder such, for example, Huntington's, Parkinson's and Alzheimer's diseases, AIDS-dementia, hepatic encephalopaty, amyotrophic lateral sclerosis, epilepsy, olivopontocerebellar atrophy, Tourette's syndrome, CNS pathology related to measles virus, infection or motor neuron disease.

The compounds of this invention can be administered to a mammalian such as a human, in a variety of dosage forms, e.g. orally, in the form of tablets, capsules, sugar or film-coated tablets, liquid solutions or suspension; rectally, in the form of suppositories; parenterally, e.g. intramuscularly, by intravenous injection or infusion.

These compounds will be preferably administered in a daily dose generally in a range from about 0.1 mg to about 25 mg per kilogram of body weight per day. A suitable dose can be administered, in sub-doses per day.

The active compound is usually administered in a pharmaceutically acceptable composition.

A pharmaceutical composition according to the invention comprises a compound of formula (I) or a pharmaceutically acceptable salt thereof as an active ingredient, in association with a pharmaceutically acceptable excipient (which can be a carrier or adiluent). The pharmaceutical compositions containing the compounds of the invention are usually prepared following conventional methods and are administered in a pharmaceutically suitable form. For example, the solid oral form may contain, together with the active compound, diluents, e.g. lactose, dextrose, cellulose, corn starch or potato starch; lubricants, e.g. silica, talc, stearic acid, magnesium or calcium stearate, and/or polyethylene glycols; binding agents, e.g. starches, arabic gums, gelatins, methylcellulose or polyvinyl pirrolidone; and, in general, non toxic and inactive substances used in pharmaceutical formulations.

These pharmaceutical preparations may be manufactured in known manner, for example, by means of mixing, granulating, tabletting, sugar-coated, or film-coating processes. The liquid dispersion for oral administration, may be e.g. syrups, emulsions or suspensions. The syrups may contain as carrier, for example, saccharose or saccharose with glycerine and/or mannitol and/or sorbitol. The suspensions and the emulsions may contain as carrier, for example, a natural gum, agar, sodium alginate, pectine or polyvinyl alcohol. The suppositories may contain together with the active compound a pharmaceutically acceptable carrier, e.g. cocoa-butter,or polyethylen glycol.

The following examples illustrate but do not limit the invention.

EXAMPLE 1

(+) Threo 1-Hydroxymethyl-1-(4-benzylpiperidin-1-yl)-2-hydroxy-2-(2-aminobenzothiazol-6-yl)-ethane A stirred solution of 20 g of (+) threo 1-p-nitrophenyl-2-amino-1,3-propanediol and 27 g of 3-benzyl-1,5-dibromopentane and 35 ml of Hünig's base in 140 ml of dimethylformamide was heated at 70° C. for 5 h.

The solvent was removed in vacuo and the residue was taken in ethylacetate and washed several times with brine.

After drying, the solvent was removed and the residue was crystallized from acetone, providing 26 g of (+) threo 1-p-nitrophenyl-2-(4-benzylpiperidin-1-yl)-1,3 propandiol, m.p. 122–124° C.

A solution of 10 g (+) threo 1-p-nitrophenyl-2-(4-benzylpiperidin-1-yl)-1,3 propandiol and 2 g of Pd/C 10% in 200 ml of ethanol was hydrogenated at normal pressure at 50° C.

After removal of the catalyst, the solution was concentrated to small volume affording 7.3 g of (+) three 1-p-aminophenyl-2-(4-benzylpiperidin-1-yl)-1,3 propandiol, m.p. 62–68° C.

To a stirred solution of 5 g of (+) three 1-p-aminophenyl-2-(4-benzylpiperidin-1-yl)-1,3 propandiol and 5.7 g of KSCN in 30 ml of glacial acetic acid was added dropwise a solution of 2.36 g of $Br_2$ in 25 ml of glacial acetic acid at room temperature.

After stirring for 4 h., the yellow suspension was filtered and the solution was poured into 100 ml of concentrated ammonium solution. The precipitated was collected by filtration and then dissolved in chloroform containing 5% of methanol.

The solution was washed with diluted ammonium solution then dried.

The solvent was removed and after crystallization from ethanol, 3.8 g of (+) three 1-Hydroxymethyl-1-(4-benzylpiperidin-1-yl)-2-hydroxy-2-(2-aminobenzothiazol-6-yl)-ethane were obtained in totally yield of 38% , m.p 170–174° C., $[\alpha]_{20}D=+28.4\pm0.5$.

EXAMPLE 2

(−) Threo 1-Hydroxymethyl-1-(4-benzylpiperidin-1-yl)-2-hydroxy-2-(2-aminobenzothiazol-6-yl)-ethane Operating as in Example 1, but employing (−) threo 1-p-nitrophenyl-2-amino-1,3-propanediol instead of (+) threo 1-p-nitrophenyl-2-amino-1,3-propanediol, the title compound was obtained in 36% yield, m.p. 171–173° C., $[\alpha]_{20}D=-28.7\pm0.5$

EXAMPLE 3

(+) Erithro 1-Hydroxymethyl-1-(4-benzylpiperidin-1-yl-²-hydroxy-2-(2-aminobenzothiazol-6-yl)-ethane Operating as in Example 1, but employing (+) erithro 1-p-nitrophenyl-2-amino-1,3-propanediol instead of (+) three 1-p-nitrophenyl-2-amino-1,3-propanediol, the title compound was obtained in 41% yield, m.p. 156–159° C., $[\alpha]_{20}D=+54.4\pm0.7$

EXAMPLE 4

(−) Erithro 1-Hydroxymethyl-1-(4-benzylpiperidin-1-yl)-2-hydroxy-2-(2-aminobenzothiazol-6-yl)-ethane Operating as in Example 1, but employing (−) erithro 1-p-nitrophenyl-2-amino-1,3-propanediol instead of (+) three 1-p-nitrophenyl-2-amino-1,3-propanediol, the title compound was obtained in 37% yield, m.p. 155–157° C., $[\alpha]_{20}D=-54.8\pm0.5$

EXAMPLE 5

(+) Threo 1-Phenoxymethyl-1-(4-benzylpiperidin-1-yl)-2-hydroxy-2-(2-aminobenzothiazol-6-yl)-ethane To a stirred solution of 5 g of (+) threo 1-p-nitrophenyl-2-(4-benzylpiperidin-1-yl)-1,3-propandiol and 2.54 g of phenol and 3.9 g of triphenylphosphine in 100 ml of THF was added dropwise at room temperature a solution of 2.98 g of diethylazodicarboxylate in 30 ml of THF. After 5 h., the solvent was removed and the residue was chromatographed on silica gel eluting with ethylacetate/cyclohexane ½ affording after crystallization from acetone 4.5 g of (+) threo 1-phenoxymethyl-1-(4-benzylpiperidin-1-yl)- 2-p-nitrophenyl-2-hydroxy-ethane, m.p. 159–162° C.

A solution of 2.5 g (+) threo 1-phenoxymethyl-1-(4-benzylpiperidin-1-yl)-2-p-nitrophenyl-2-hydroxy-ethane and 0.5 g of Pd/C 10% in 25 ml of ethanol was hydrogenated at normal pressure at 30° C. After removal of the catalyst, the solution was concentrated to small volume affording 1.7 g of (+) threo 1-phenoxymethyl-1-(4-benzylpiperidin-1-yl)-2-p-aminophenyl-2-hydroxy-ethane, m.p. 146–147° C.

To a stirred solution of 1.5 g of (+) three 1-phenoxymethyl-1-(4-benzylpiperidin-1-yl)-2-p-aminophenyl-2-hydroxy-ethane and 1.43 g of KSCN in 20 ml of glacial acetic acid was added dropwise a solution of 0.58 g of $Br_2$ in 5 ml of glacial acetic acid at room temperature. After stirring for 2 h., the yellow sospension was filtered and the solution was poured into 70 ml of concentrated ammonium solution. The cloudy basic solution was extracted with ethyl acetate dried and evaporated. The resulting yellow residue was chromatographed on silica gel eluting with ethylacetate/cycloexane ⅓, furnishing after crystallization from ethanol 0.9 g of the title compound, m.p. 210–214° C., $[\alpha]_{20}D=-2.1\pm0.1$

EXAMPLE 6

(+) Threo 1-Dimethylaminomethyl-1-(4-benzylpiperidin-1-yl)-2-hydroxy-2-(2-aminobenzothiazol-6-yl)-ethane To a stirred solution of 10 g of (+) threo 1-p-nitrophenyl-2-(4-benzylpiperidin-1-yl)-1,3-propanediol and g of phthalimide and g of triphenylphosphine in 200 ml of THF was added dropwise at room temperature a solution of g of diethylazodicarboxylate in 50 ml of THF. After stirring for 4 h., to the resulting reaction mixture was added 30 ml of hydrazine hydrate 90% and the stirring was continued 4 h. After removal of the precipitated phthalazin-2,4-dione, the solvent was removed and the residue taken up in ethylacetate was thoroughly washed with 1 M hydrochloric acid solution.

The water solution was then strongly basified with concentrate ammonium hydroxide solution and extracted with chloroform. After drying the solvent was removed and the residue was crystallized from a small volume of ethanol affording 7.3 g of (+) threo 1-(p-nitrophenyl)-2-4-benzylpiperidin-1-yl)-3-aminopropan-1-ol, m.p. 152–155° C.

To a solution of 3.5 g of (+) threo 1-(p-nitrophenyl)-2-(4-benzylpiperidin-1-yl)-1-aminopropan-1-ol in 35 ml of ethanol and 9 ml of 2 M hydrochloric acid and 5 ml of formaldehyde 40% solution was added portionwise 1.1 g or sodiumcyanoborohydride. After stirring 1 h, the solution was diluted with ethylacetate and basified with a concentrated ammonium hydroxide solution. The organic phase was dried and the solvent removed, affording 3.8 g of (+) threo 1-(p-nitro-phenyl)-2- (4-benzylpiperidin-1-yl) -3-dimethylaminopropan-1-ol, m.p. 132–135° C.

A solution of 5 g (+) threo 1-(p-nitro-phenyl)-2-(4-benzylpiperidin-1-yl)-3-dimethylaminopropan-1-ol and 0.5 g of Pd/C 10% in 50 ml of ethanol was hydrogenated at normal pressure at 50° C. After removal of the catalyst, the solution was concentrated to small volume affording 3.1 g of (+) threo 1-(p-amino-phenyl)-2-(4-benzylpiperidin-1-yl) -3-dimethylaminopropan-1-ol, m.p. 121–125° C.

To a stirred solution of 3.4 g of (+) threo 1-(p-amino-phenyl)-2-(4-benzylpiperidin-1-yl)-1-dimethylaminopropan-1-ol and 3.6 g of KSCN in 50 ml of glacial acetic acid was added dropwise a solution of 1.5 g of $Br_2$ in 25 ml of glacial acetic acid at room temperature.

After stirring for 2 h., the yellow sospension was filtered and the solution was poured into 100 ml of concentrated ammonium solution. The cloudy basic solution was extracted with ethyl acetate dried and evaporated. The residue was chromatographed on silica gel elutin with ethylacetate/cyclohexane 1/1, affording 1.8 g of the title compound, m.p. 116–120° C.,. , $[\alpha]_{20}D=-12.3\pm0.5$.

EXAMPLE 7

(+) Threo 1-Benzoylaminomethyl-1-(4-benzylpiperidin-1-yl)-2-hydroxy-2-(2-aminobenzothiazol-6-yl)-ethane To a solution of 5 g of (+) threo 1-(p-nitrophenyl)-2-(4-benzylpiperidin-1-yl)-3-aminopropan-1-ol in 50 ml of pyridine was added dropwise 0.32 ml of benzoyl chloride dissolved in 5 ml of pyridine. After stirring 30 minutes, the solution was diluted with ethylacetate and washed with brine. The organic phase was dried and the solvent removed, affording after crystallization from acetone 5.2 g of (+) threo 1-(p-nitro-phenyl)-2-(4-benzylpiperidin-1-yl)-3-benzoylaminopropan-1-ol, m.p. 143–147° C.

A solution of 3 g (+) threo 1-(p-nitro-phenyl)-2-(4-benzylpiperidin-1-yl)-3 benzoylaminopropan-1-ol and 0.5 g of Pd/C 10% in 50 ml of ethanol was hydrogenated at normal pressure at 50° C. After removal of the catalyst, the solution was concentrated to small volume affording 1.7 g of (+) threo 1-(p-amino-phenyl)-2-(4-benzylpiperidin-1-yl)-1-benzoylaminopropan-1-ol, m.p. 126–129° C.

To a stirred solution of 5.3 g of (+) threo 1-(p-amino-phenyl)-2-(4-benzylpiperidin-1-yl)-3-benzoylaminopropan-1-ol and 4.6 g of KSCN in 100 ml of glacial acetic acid was added dropwise a solution of 1.95 g of Br2 in 25 ml of glacial acetic acid at room temperature. After stirring for 2 h., the yellow sospension was filtered and the solution was poured into 100 ml of concentrated ammonium solution. The cloudy basic solution was extracted with ethyl acetate dried and evaporated. The residue was chromatographed on silica gel elutin with ethylacetate/cyclohexane ½, providing providing 3.7 g of the title compound, m.p. 160–162° C., $[\alpha]_{20}D=+20.3\pm0.5$.

EXAMPLE 8

(+) Threo 1-Methanesulphonylaminomethyl-1-(4-benzylpiperidin-1-yl)-2-hydroxy-2-(2-aminobenzothiazol-6-yl)-ethane Operating as in Example 7, but employing (+) threo 1-(p-amino-phenyl)-2-(4-benzylpiperidin-1-yl)-1-methansulphonylaminopropan-1-ol, instead of (+) threo 1-(p-amino-phenyl)-2-(4-benzylpiperidin-1-yl)-1-benzoylaminopropan-1-ol, the title compound was obtained, m.p. 158–160° C., $[\alpha]_{20}D=-10.4\pm0.5$.

EXAMPLE 9

(+) Threo 1-Phenylsulphonylaminomethyl-1-(4-benzylpiperidin-1-yl)-2-hydroxy-2-(2-aminobenzothiazol-6-yl)-ethane Operating as in Example 7, but employing (+) threo 1-(p-amino-phenyl)-2-(4-benzylpiperidin-1-yl)-1- phenylsulphonylaminopropan-1-ol, instead of (+) threo 1-(p-amino-phenyl)-2-(4-benzylpiperidin-1-yl)-1-benzoylaminopropan-1-ol, the title compound was obtained, 204–206° C., $[\alpha]_{20}D=-18.3\pm0.4$.

EXAMPLE 10

(1 S, 2 R) 1-(2-Amino-benzothiazol-6-yl)-2-(4-benzyl-piperidin-1-yl)-propan-1-ol To stirred solution of 25 g of (−) threo 1-p-nitrophenyl-2-(4-benzylpiperidin-1yl)-1,3-propanediol and 43 g of diphenyldisulfide in 100 ml of dioxane was added dropwise 42 g of (n-but.) 3P and the resulting cloudy solution was heated at reflux for 5 hours. The solvent was removed and the resulting oil was chromatographed on silica gel eluting with ethylacetate/cyclohexane ⅖ affording after crystallization from a small volume of acetone 5.3 g of (−) threo 1-p-nitrophenyl-2-(4-benzyl-piperidin-1-yl)-1,3-dithiophenyl-propane, m.p. 156–159° C.

Continuing the elution with ethylacetate/cyclohexane ½ followed by crystallization from ethanol, 23.4 g of (−) threo 1-p-nitrophenyl-2-(4-benzyl-piperidin-1-yl)-3-thiophenyl-propan-1-ol were recovered, m.p. 124–126° C. To a solution of 10 g of (−) three 1-p-nitrophenyl-2-(4-benzyl-piperidin-1-yl)-3-thiophenyl-propan-1-ol in 150 ml of refluxing ethanol were added portionwise, under nitrogen, 20 g of washed Ni-Raney. After 30 minutes at reflux, the suspension was filtered and the solvent was removed, crystallization from a small volume of ethanol furnished 4.8 g of (−) 1-p-aminophenyl-2-(4-benzyl-piperidin-1-yl)-propan-1-ol, m.p. 104–107° C.

To a stirred solution of 4 g of 1-p-aminophenyl-2-(4-benzyl-piperidin-1-yl)-propan-1-ol and 4.6 g of KSCN in 35 ml of glacial acetic acid was added dropwise 3.8 g of Br2 in 10 ml of glacial acetic acid. After 5 hours, the yellow suspension was filtered and the solution was poured into 100 ml of a concentrated hydroxide ammonium solution. After extraction with ethylacetate, the organic phase was washed with brine and dried. The solvent was removed and the residue was filtered on a small of silica gel eluting with acetone/cyclohexane ¼, affording 2.2 g of the title compound, m.p. 197–200° C., $[\alpha]_{20}D=-15.6\pm0.2$.

EXAMPLE 11

(1 R, 2 S) 1-(2-Amino-benzothiazol-6-yl)-2-(4-benzyl-piperidin-1-yd)-propan-1-ol Operating as in Example 10, but employing (+) threo 1-p-nitrophenyl-2-(4-benzylpiperidin-1yl)-1,3-propanediol instead of (−) threo 1-p-nitrophenyl-2-amino-1,3-propanediol, the title compound was obtaine, m.p. 198–201° C., $[\alpha]_{20}D=+15.4\pm0.3$.

EXAMPLE 12

(1 R, 2 R) 1-(2-Amino-benzothiazol-6-yl)-2-(4-benzyl-piperidin-1-yl)-propan-1-ol Operating as in Example 10, but employing (+) erithro 1-p-nitrophenyl-2-(4-benzylpiperidin-1yl)-1,3-propanediol instead of (−) threo 1-p-nitrophenyl-2-amino-1,3-propanediol, the title compound was obtained, m.p. 208–211° C., $[\alpha]_{20}D=-25.2\pm0.4$

EXAMPLE 13

(1 R) 1-(2-Amino-benzothiazol-6- yl)-2-(4-benzyl-piperidin-1-yl)-propane hydrochloride Operating as in Example 10, but employing (−) erithro 1-p-nitrophenyl-2-(4-benzyl-piperidin-1-yl)-1,3-dithiophenyl-propane instead of (−) threo 1-p-nitrophenyl-2-(4-benzyl-piperidin-1-yl)-3-thiophenyl-propan-1-ol, the title compound was obtained, m.p. 151–153° C., $[\alpha]_{20}D=+25.6\pm0.4$

EXAMPLE 14

(1 S) 1-(2-Amino-benzothiazol-6-yl)-2-(4-benzyl-piperidin-1-yl)-propane hydrochloride Operating as in Example 10, but employing (+) erithro 1-p-nitrophenyl-2-(4-benzyl-piperidin-1-yl)-1,3-dithiophenyl-propane instead of (+) threo 1-p-nitrophenyl-2-(4-benzyl-piperidin-1-yl)-3-thiophenyl-propan-1-ol, the title compound was obtained, m.p. 152–154° C., $[\alpha]_{20}D=+12.3\pm0.2$

EXAMPLE 15

1-(2-Amino-benzothiazol-6-yl)-2-(4-benzyl-piperidin-1-yl)-ethane

A solution of 3 g of 1-(2-Acetylamino-benzothiazol-6-yl)-2-bromo-ethane and 1.95 g of 4- benzylpiperidin and 3.5 g of $K_2CO_3$ in 20 ml of DME was heated at 75° C. for 2 hours. The solution was diluted with ethylacetate and washed with brine, after removal of the solvent the residue was heated at reflux in 50 ml of ethanol containing 5 ml of 5 M NaOH for 1 hour. The solvent was evaporated and the residue taken up in ethylacetate was washed with brine and dried. After removal of the solvent, the reaction produce was chromatographed on silica gel eluting with ethylacetate/cyclohexane ⅓ affording the title compound in 67% yield, m.p. 152–153° C.

EXAMPLE 16

1-(2-Amino-benzothiazol-6-yl)-2-(4-phenoxy-piperidin-1-yl)-ethane

Operating as in example 15, but employing 4-phenoxy-piperidine instead of 4-benzyl-piperidine, the title compound was obtained in 75% yield, m.p. 164–167° C.

EXAMPLE 17

1-(2-Amino-benzothiazol-6-yl)-2-(4-phenylthio-piperidin-1-yl)-ethane

Operating as in example 15, but employing 4-thiophenoxy-piperidine instead of 4-benzyl-piperidine, the title compound was obtained in 55% yield, m.p. 145–1148° C.

EXAMPLE 18

1-(2-Amino-benzothiazol-6-yl)-2-(4-benzoyl-piperidin-1-yl) ethane

Operating as in example 15, but employing 4-benzoyl-piperidine instead of 4-benzyl-piperidine, the title compound was obtained in 55% yield, m.p. 186–188° C.

EXAMPLE 19

1-(2-Amino-benzothiazol-6-yl)-2-(4-(4,4'-difluorodiphenylmethyl-piperidin-1-yl) -ethane Operating as in example 15, but employing 4-(4,4'-difluorodiphenylmethyl benzoyl-piperidine instead of 4-benzyl-piperidine, the title compound was obtained in 73% yield, m.p. 204–209° C.

EXAMPLE 20

(+) 1-(2-Amino-benzothiazol-6-yl)-3-phenoxy-2-(4-benzyl-piperidin-1-yl)-propan-1-one To a stirred solution of 2 ml of DMSO in 50 ml of dichloromethane at −78° C. was added dropwise a solution 3.8 g of trifluoroacetic anhydride in 10 ml of dichloromethane.

After stirring for 20 min., a solution of 3 g of (±) threo 1-phenoxymethyl-1-(4-benzylpiperidin-1-yl)-2-hydroxy-2-(2-aminobenzothiazol-6-yl)-ethane in 30 ml of dichloromethane was slowly added dropwise and the resulting cloudy solution was stirred for 20 min.

Then, a solution of 4 ml of TEA in 10 ml of dichloromethane was added and the stirring was continued for 20 min. The resulting solution was washed with 1 M $Na_2CO_3$ solution and dried.

Removal of the solvent and crystallization from a small volume of ethanol afforded 2.3 of the title compound, m.p. 189–193° C.

According to the following procedure, the below listed compounds can be prepared:
- (±) 1-(2-Amino-benzothiazol-6-yl)-3-dimethylamino-2-(4-benzyl-piperidin-1-yl)-propan-1-one;
- (±) 1-(2-Amino-benzothiazol-6-yl)-3-benzoylamino-2-(4-benzyl-piperidin-1-yl)-propan-1-one;
- (±) 1-(2-Amino-benzothiazol-6-yl)-3-methanesulphonylamino-2-(4-benzyl-piperidin-1-yl)-propan-1-one;
- (±) 1-(2-Amino-benzothiazol-6-yl)-3-phenylsulphonylamino-2-(4-benzyl-piperidin-1-yl)-propan-1-one;
- (±) 2-(4-Benzylpiperidin-1-yl)-1-(2-amino-benzothiazol-6-yl)-propan-1-one; and
- (±) 2-(4-Benzoylpiperidin-1-yl)-1-(2-amino-benzothiazol-6-yl)-propan-1-one.

EXAMPLE 21

1-(2-Amino-benzothiazol-6-yl)-2-(4-benzyl-piperidin-1-yl)-ethanone

A solution of 2 g of 1-(2-Acetylamino-benzothiazol-6-yl)-2-bromo-ethanone and 1.5 g of 4-benzylpiperidin and 2.5 g of $K_2CO_3$ in 20 ml of DMF was heated at 35° C. for 2 hours.

The solution was diluted with ethylacetate and washed with brine, after removal of the solvent, the residue dissolved in 50 ml of ethanol containing 3 ml of 5 M NaOH was heated at 50° C. for 1 hour. The solvent was evaporated and the residue taken up in ethylacetate was washed with brine and dried. After removal of the solvent, the reaction product was chromatographed on silica gel eluting with ethylacetate/cyclohexane ⅓ affording the title compound in 53% yield, rmp. 182–185° C.

According to the following procedure, the below listed compounds can be prepared:
- 1-(4-Benzoylpiperidin-1-yl)-2-(2-amino-benzothiazol-6-yl)-ethanone; and
- 1-(4-Phenoxypiperidin-1-yl)-2-(2-amino-benzothiazol-6-yl)-ethanone.

EXAMPLE 22

With the usual methods of pharmaceutical technique, preparation can be made of tablets having the following composition:

| | |
|---|---|
| Compound of Example 15 | 15 mg |
| Lactose | 80 mg |
| Starch (maize) | 10 mg |
| Magnesium Stearate | 5 mg |
| Tablet Weigh | 110 mg |

What is claimed is:
1. A compound of formula (I)

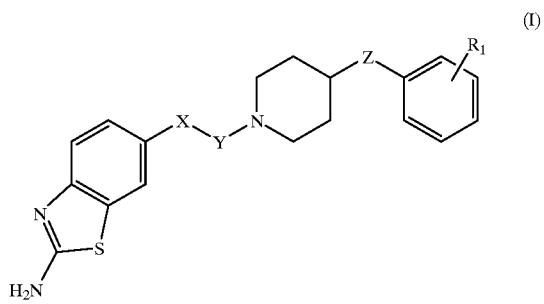

as a single isomer or as a mixture of isomers,
wherein

X is CO, C=NOH, CHOH or $CH_2$;

Y is $CH_2$ or $CHCH_2R_2$ in which
$R_2$ is hydrogen, hydroxy, phenoxy, amino, $N(CH_3)_2$, $OCOR_4$ in which $R_4$ is $C_1$–$C_6$ alkyl or a group of formula (i)

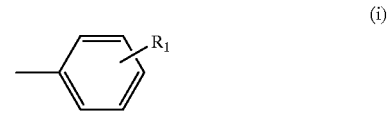

wherein $R_1$ is hydrogen, halogcen, cyano, a linear or branched $C_1$–$C_5$ alkyl group, a linear or branched $C_1$–$C_5$ alkoxy group or trifluoromethyl; or $R_2$ is $NHR_3$ in which $R_3$ is a linear or branched $C_2$–$C_6$ alkanoyl group, a linear or branched $C_1$–$C_6$ alkylsulfonyl group, trifluoromethanesulfonyloxy, or a group of formula (ii) or (iii)

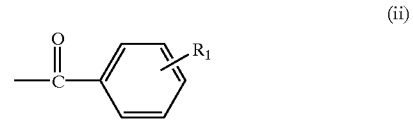

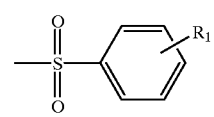

wherein $R_1$ is as defined above;

Z is a $(CH_2)_n$ group wherein n is zero or an integer from 1 to 4; CHOH; CO; O; S; $SO_2$ or a group of formula (iv)

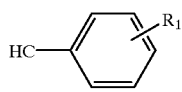

wherein $R_1$ is as defined above;
provided that:
  when X is CO, $R_2$ is not hydroxy;
or a pharmaceutically acceptable salt thereof.

2. A compound as claimed in claim 1 wherein
X is CO, CHOH or $CH_2$;
Y is $CH_2$ or $CHCH_2R_2$ wherein $R_2$ is hydrogen, hydroxy, phenoxy, $N(CH_3)_2$ or wherein $R_2$ is $NHR_3$ in which $R_3$ is a linear $C_1$–$C_3$ alkylsulfonyl group, a group of formula (ii) or (iii) as defined above in which $R_1$ is hydrogen;
Z is a $(CH_2)_n$ group wherein n is 1, CO, O, S or a group of formula (iv) as defined above in which $R_1$ is hydrogen or halogen;
$R_1$ is as defined above;
provided that:
  when X is CO, $R_2$ is not hydroxy.

3. A compound selected from the group consisting of:
1) 1-Hydroxymethyl-1-(9-benzylpiperidin-1-yl)-2-hydroxy-2-(2-aminobenzothiazol-6-yl)-ethane;
2) 1-Phenoxymethyl-1-(9-benzylpiperidin-1-yl )-2-hydroxy-2-(2-aminobenzothiazol-6-yl)-ethane;
3) 1-Dimethylaminomethyl-1-(9-benzylpiperidin-1-yl)-2-hydroxy-2-(2-aminobenzothiazol-6-yl)-ethane;
4) 1-Benzoylaminomethyl-1-(4-benzylpiperidin-1-yl)-2-hydroxy-2-(2-aminobenzothiazol-6-yl)-ethane;
5) 1-Methanesulphonylaminomethyl-1-(4-benzylpiperidin-1-yl)-2-hydroxy-2-(2-aminobenzothiazol-6-yl)-ethane;
6) 1-Phenylsulphonylaminomethyl-1-(4-benzylpiperidin-1-yl)-2-hydroxy-2-(2-aminobenzothiazol-6-yl)-ethane;
7) 1-(2-Amino-benzothiazol-6-yl)-2-(4-benzyl-piperidin-1-yl)-propan-1-ol;
8) 1-(2-Amino-benzothiazol-6-yl)-2-(4-benzyl-piperidin-1-yl)-propane;
9) 1-(-Amino-benzothiazol-6-yl)-2-(4-benzyl-piperidin-1-yl)-ethane;
10) 1-(2-Amino-benzothiazol-6-yl)-2-(4-phenoxy-piperidin-1-yl)-ethane;
11) 2-(2-Amino-benzothiazol-6-yl)-2-(4-phenylthio-piperidin-1-yl)-ethane;
12) 1-(2-Amino-benzothiazol-6-yl)-2-(4-benzoyl-piperidin-1-yl)-thane;
13) 1-(2-Amino-benzothiazol-6-yl)-2-(4-(4,4'-difluorodiphenylmethyl-piperidin-1-yl)-ethane;
14) 1-(2-Amino-benzothiazol-6-yl)-3-phenoxy-2-(4-benzyl-piperidin-1-yl)-propan-1-one;
15) 1-(2-Amino-benzothiazol-6-yl)-3-dimethylamino-2-(4-benzyl-piperidin-1-yl)-propan-1-one;
16) 1-(2-Amino-benzothiazol-6-yl)-3-benzoylamino-2-(4-benzyl-piperidin-1-yl)-propan-1-one;
17) 1-(2-Amino-benzothiazol-6-yl)-3-methanesulphonylamino-2-(4-benzyl-piperidin-1-yl)-propan-1-one;
18) 1-(2-Amino-benzothiazol-6-yl)-3-phenylsulphonylamino-2-(4-benzyl-piperidin-1-yl)-propan-1-one;
19) 2-(4-Benzylpiperidin-1-yl)-1-(2-amino-benzothiazol-6-yl)-propan-1-one;
20) 2-(2-Benzoylpiperidin-1-yl)-1-(2-aminobenzothiazol-6-yl)-propan-1-one;
21) 1-(2-Aminobenzothiazol-6-yl)-2-(4-benzyl-piperidin-1-yl)-ethanone;
22) 1-(4-Benzoylpiperidin-1-yl)-2-(2-amino-benzothiazol-6-yl)-ethanone;
23) 1-(4-Phenoxypiperidin-1-yl)-2-(2-amino-benzothiazol-6-yl)-ethanone; their racemates, optical isomers and pharmaceutically acceptable salts thereof.

4. A process for preparing a compound as defined in claim 1 which comprises:
a) reacting a compound of formula (II)

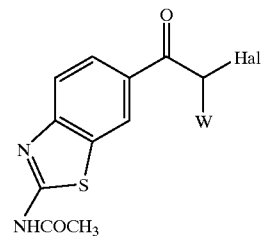

either as a pure optical isomer or as a racemic mixture, wherein W is hydrogen or methyl and Hal is a halogen atom;
with a compound of formula (III)

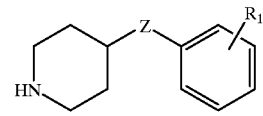

wherein
Z is a $(CH_2)_n$ group wherein n is zero or an integer from 1 to 4, CHOH, CO, O, S, $SO_2$ or a group of formula (iv)

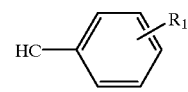

wherein $R_1$ is hydrogen, halogen, cyano, a linear or branched $C_1$–$C_5$ alkyl group, a linear or branched $C_1$–$C_5$ alkoxy group or trifluoromethoxy; to obtain a compound of formula (I) as a pure optical isomer or as racemic mixture, wherein Z and $R_1$ are as defined above, X is CO and Y is $CH_1$ or $CHCH_2R_2$ in which $R_2$ is hydrogen;
and, if desired, b) converting a compound of formula (I) as obtained under step a), into another compound of formula (I) wherein Y, Z and $R_1$ are as defined above and X is CHOH; or c) converting a compound of formula (I) as obtained under step a), into another compound of formula (I) wherein Y, Z and $R_1$ are as defined above and X is $CH_2$; or d) converting a compound of formula (I) as obtained under step a), into another compound of formula (I) wherein Y, Z and $R_1$ are as defined above and X is C=NOH; or e) condensing a compound of formula (IV)

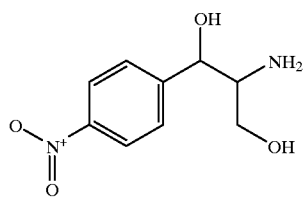

(IV)

as a pure optical isomer or as a racemic mixture, with a compound of formula (V)

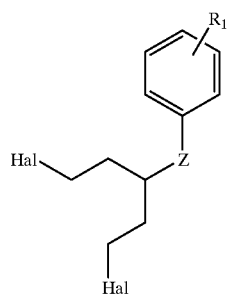

(V)

wherein Hal, Z and $R_1$ are as defined above, to obtain a compound of formula (VI)

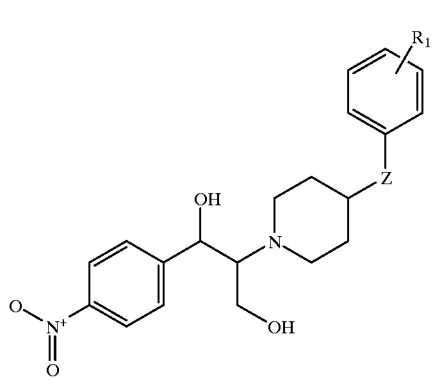

(VI)

as a pure optical isomer or as a racemic mixture, wherein Z and $R_1$ are as defined above;

f) converting a compound of formula (VI) as obtained under step e), to obtain a compound of formula (VII)

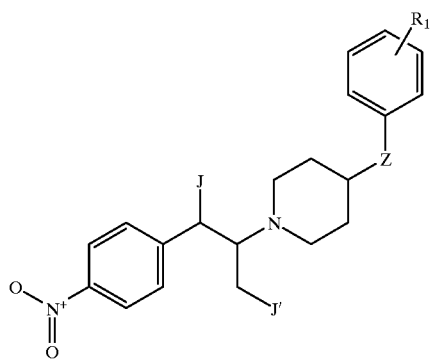

(VII)

as a pure optical isomer, as a racemic mixture, wherein Z and $R_1$ are as defined above, J is hydroxy or phenylthio and J' is amino, $N(CH_3)_2$ phenoxy, phenylthio, $OCOR_4$ in which $P_4$ is $C_1$–$C_6$ alkyl or a group of formula (i)

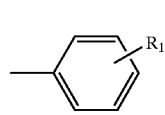

(i)

wherein $R_1$ is as defined above, or J' is $NHR_3$ in which $R_3$ is a linear or branched $C_2$–$C_6$ alkanoyl group, a linear or branched $C_1$–$C_6$ alkylsulfonyl group, trifluoromethanesulphonyloxy or a group of formula (ii) or (iii)

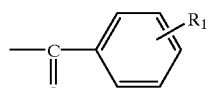

(ii)

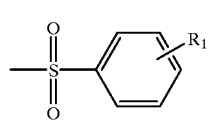

(iii)

wherein $R_1$ is as defined above;

g) reducing a compound of formula (VII) to obtain a compound of formula (VIII)

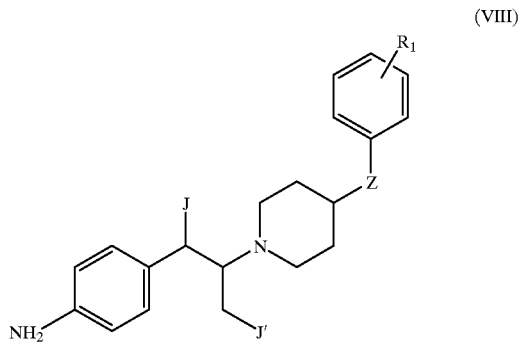

(VIII)

as a pure optical isomer or as a racemic mixture, wherein J is hydroxy or hydrogen, Z and $R_1$ are as defined above and J' is hydrogen, phenoxy, $N(CH_3)_2$, $OCOR_4$ in which $R_4$ is as defined above, or J' is $NHR_3$ in which $R_3$ is as defined above;

h) converting a compound of formula (VIII) into a compound of formula (I), as a pure optical isomer or as a racemic mixture, wherein Z and $R_1$ are as defined above, X is CHOH or $CH_2$ and Y is $CHCH_2R_2$ in which $R_2$ is hydrogen, phenoxy, $N(CH_3)_2$, $OCOR_4$ in which $R_4$ is as defined above, or J' is $NHR_3$ in which $R_3$ is as defined above; and, if desired, i) converting a compound of formula (I) as a pure optical isomer or as a racemic mixture, wherein Z, $R_1$ and X are as defined above and Y is $CHCH_2R_2$ wherein $R_2$ is $NHR_3$ in which $R_3$ is a linear or branched $C_2$–$C_6$ alkanoyl group or a group of formula (ii) as defined above, into another compound of formula (I) wherein Z, $R_1$ and X are as defined above and Y is $CHCH_2R_2$ wherein $R_2$ is amino, and, if desired, j) converting a compound of formula (I) as obtained under step h) or i) into another compound of formula (I) wherein Y, Z and $R_1$ are as defined above and X is C=O;

and, if desired, converting a compound of formula (I) into a pharmaceutically acceptable salt thereof.

5. A method for treatment of an acute or a chronic neurodegenerative disease, comprising administering to a subject in need thereof an effective antineurodegenerative amount of a compound of claim 1.

6. The method of claim 5 wherein the acute neurodegenerative disease is ischemia, hypoglycemia or hypoxia.

7. The method of claim 5 wherein the chronic neurodegenerative disease is Huntington's disease, Parkinson's disease Alzheimer's disease, AIDS-dementia, hepatic encephalopaty, amyotrophic lateral sclerosis, epilepsy, olivopontocerebellar atrophy, Tourette's syndrome, CNS pathology related to measles virus, infection or motor neuron disease.

8. A pharmaceutical composition which comprises, as an active ingredient, a compound as defined in claim 1 and a pharmaceutically acceptable excipient.

* * * * *